(12) United States Patent
Unger et al.

(10) Patent No.: US 10,279,053 B2
(45) Date of Patent: May 7, 2019

(54) MICROBUBBLE COMPOSITIONS, METHOD OF MAKING SAME, AND METHOD USING SAME

(75) Inventors: Evan C. Unger, Tucson, AZ (US); Patrick W. Hendon, Tucson, AZ (US)

(73) Assignee: NuvOx Pharma LLC, Tucson, AZ (US)

( * ) Notice: Subject to any disclaimer, the term of this patent is extended or adjusted under 35 U.S.C. 154(b) by 1450 days.

(21) Appl. No.: 13/186,373

(22) Filed: Jul. 19, 2011

(65) Prior Publication Data
US 2013/0022550 A1    Jan. 24, 2013

(51) Int. Cl.
*A61K 49/22* (2006.01)

(52) U.S. Cl.
CPC .................. *A61K 49/223* (2013.01)

(58) Field of Classification Search
CPC .............................. A61K 49/22; A61K 49/223
See application file for complete search history.

(56) References Cited

U.S. PATENT DOCUMENTS

| | | | |
|---|---|---|---|
| 4,310,505 A | 1/1982 | Baldeschwieler et al. | |
| 4,572,203 A | 2/1986 | Feinstein | |
| 4,718,433 A | 1/1988 | Feinstein | |
| 4,774,958 A | 10/1988 | Feinstein | |
| 4,957,656 A | 9/1990 | Cerny et al. | |
| 5,276,146 A | 1/1994 | Breillatt, Jr. et al. | |
| 5,344,930 A | 9/1994 | Riess et al. | |
| 5,562,893 A | 10/1996 | Lohrmann | |
| 6,537,246 B1 * | 3/2003 | Unger et al. | 604/82 |
| 6,548,047 B1 | 4/2003 | Unger | |
| 7,677,419 B2 * | 3/2010 | DiGregorio | A61M 5/3129 222/386 |
| 2002/0129656 A1 | 9/2002 | Tsuzuki | |
| 2006/0257321 A1 | 11/2006 | Schneider et al. | |

FOREIGN PATENT DOCUMENTS

| | | | | |
|---|---|---|---|---|
| EP | 1228770 A1 | | 8/2002 | |
| EP | 1550464 A1 | | 7/2005 | |
| WO | WO 1998016210 | * | 4/1998 | ............ A61K 31/02 |
| WO | 2000072757 A1 | | 12/2000 | |

OTHER PUBLICATIONS

PCT/US2012/047441—International Search Report and Written Opinion dated Jan. 29, 2013.

* cited by examiner

*Primary Examiner* — Michael G. Hartley
*Assistant Examiner* — Leah H Schlientz
(74) *Attorney, Agent, or Firm* — Milstein Zhang & Wu LLC

(57) ABSTRACT

A method of forming a plurality of microbubbles, wherein the method disposes in a sealed container comprising a first volume at ambient pressure, a second volume of a mixture comprising one or more microbubble stabilizing materials. The first volume is greater than said second volume. The method further comprises sealing said container, introducing a gas into said sealed container, and shaking the container to form said plurality of microbubbles.

10 Claims, 3 Drawing Sheets

MICROBUBBLE COMPOSITIONS, METHOD OF MAKING SAME, AND METHOD USING SAME

TECHNICAL FIELD

The present invention relates to microbubble compositions that are useful as ultrasonic contrast agents for medical imaging, for targeted delivery of diagnostics or therapeutic agents and a method of making and using said microbubble compositions.

BACKGROUND ART

Acoustic-based imaging techniques are used in both diagnostic and therapeutic procedures. Contrast agents are often used with acoustic-based imaging techniques to enhance image quality. Contrast agents are able to increase acoustic backscatter, create an ultrasonic echo, and create resonance effects, resulting in high echogenicity. Materials with high echogenicity are better able to return a signal when exposed to an acoustic wave. The increased echogenic difference between the contrast agent and the surrounding material increases the signal contrast difference and is used to create higher resolution images.

Gas filled microbubbles are often used as contrast agents. The microbubbles are generally less than one millimeter in diameter. But, in many acoustic-based imaging applications, the microbubble diameter is less than 6 micrometers, which is smaller than the size of red blood cells and allows the microbubbles to freely flow through the entire circulatory system.

In some instances, simple air bubbles are used. The surface of the air bubble reflects the acoustic waves and the gas core of the bubble may compress in the acoustic field to generate an echo. Air bubbles, however, have relatively short useful lifespans because the water-soluble gases in air leak into the surrounding solution. To increase the useful life, bubbles may be filled with heavy gases that are less water-soluble.

Ultrasound contrast agents are approved by the United States Food and Drug Administration (FDA) for medical imaging. Presently, there are two such agents approved by the FDA in the United States. Both of these agents are based on perfluoropropane gas. One is coated by phospholipid; the other is coated by serum albumin. In Europe, clinical trials are under way with an agent based on phospholipid-coated perfluorobutane microbubbles.

SUMMARY OF THE INVENTION

A method of forming a plurality of microbubbles, wherein the method disposes in a sealed container comprising a first volume at ambient pressure, a second volume of a mixture comprising one or more microbubble stabilizing materials. The first volume is greater than said second volume. The method further comprises sealing said container, introducing a gas into said sealed container, and shaking the container to form said plurality of microbubbles.

A contrast agent composition for medical imaging is presented. The contrast agent comprises a plurality of microbubbles, wherein each microbubble comprises a shell encapsulating a gas bubble, wherein the gas bubble is selected from the group consisting of perfluorobutane, perfluoropentane, and perfluorohexane, and each of the plurality of microbubbles comprises a diameter less than about 1.25 microns.

A contrast agent composition for medical imaging formed by a process is presented. The process disposes in a sealed container comprising a first volume, a second volume of a mixture comprising one or more microbubble stabilizing materials in combination with a liquid having a boiling point less than about 57° C. at 760 mm pressure, wherein said first volume is greater than said second volume. The method then volatizes the liquid by reducing the pressure in the sealed container, and shakes the container to form the contrast agent.

BRIEF DESCRIPTION OF THE DRAWINGS

The invention will be more fully understood by referring to the following Detailed Description of Specific Embodiments in conjunction with the Drawings, of which.

DETAILED DESCRIPTION OF SPECIFIC EMBODIMENTS

Figure 1:
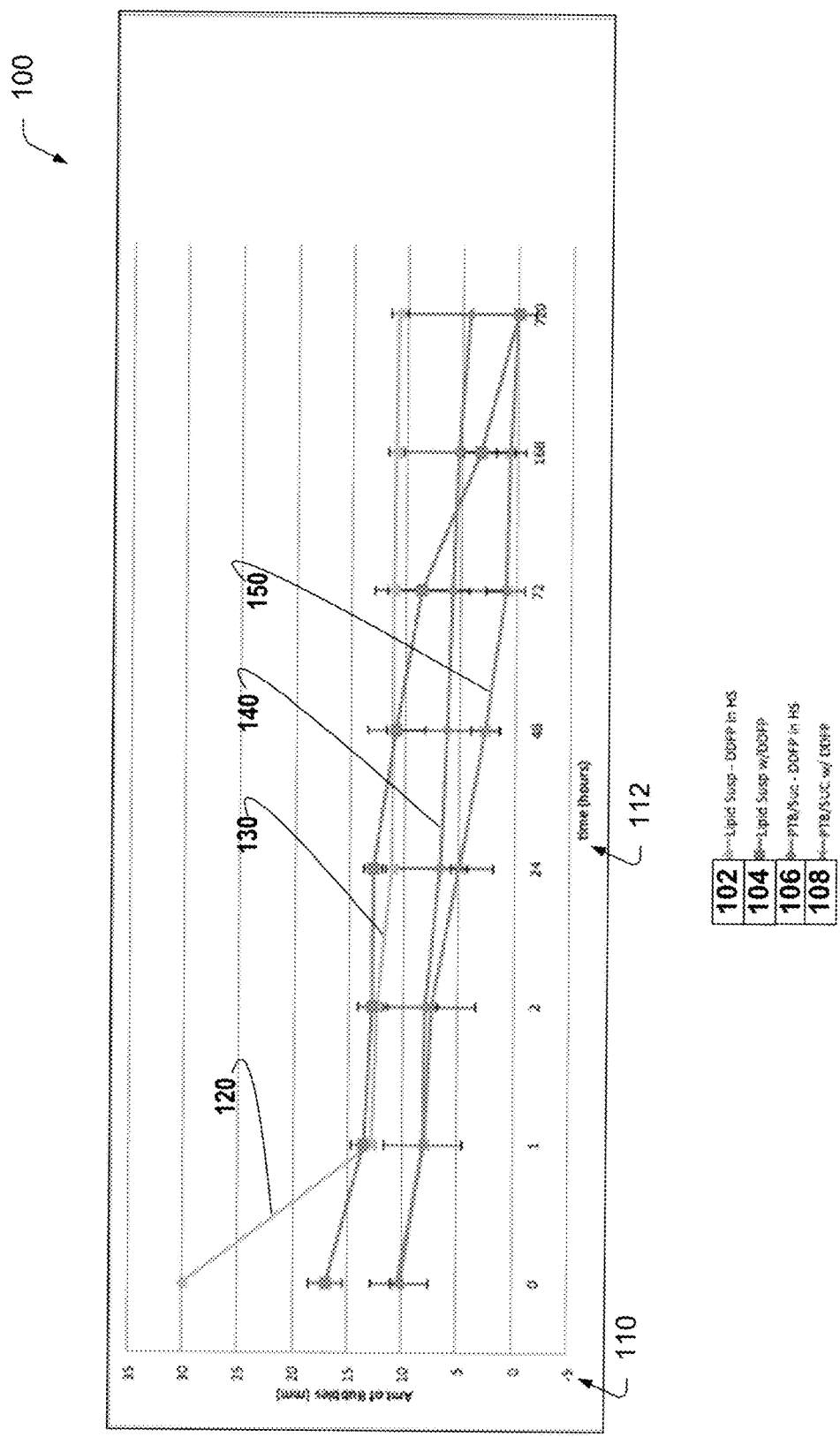
FIG. 1 graphically compares the stability over time of microbubbles comprising various compositions and formed by differing methods.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

As shown in Table 1, oxygen and nitrogen have relatively low molecular weights and are also relatively water-soluble. Note that Ostwald's coefficient is a unit-free constant that is positively correlated to aqueous solubility. The fluorinated gases have higher molecular weights and are much less water soluble than oxygen or nitrogen; much better enabling the preparation of microbubbles for ultrasound imaging.

TABLE 1

Potential Compounds for Making Gaseous Cores of Microbubbles

| Compound | Molecular Weight | Aqueous Solubility (Ostwald's Coefficient) | Boiling Point °C |
|---|---|---|---|
| Nitrogen | 28 | 18071 | -196 |
| Oxygen | 32 | 4865 | -183 |
| Sulfur Hexafluoride | 146 | 5950 | -64 |
| Perfluoropropane | 188 | 583 | -36.7 |
| Perfluorobutane | 238 | <500 | -1.7 |
| Perfluoropentane | 288 | >24 and <500 | 29 |
| Perfluorohexane | 338 | 24 | 56.6 |

It appears that perfluorobutane based microbubbles are more stable in the blood stream to static and acoustic pressure than perfluoropropane filled microbubbles. Prior art attempts to prepare ultrasound contrast agent based on perfluoropentane were unsuccessful. These prior compositions comprised an emulsion of liquid droplets of perfluoropentane stabilized with surfactant. After the material was injected intravenously the perfluoropentane remained in the liquid state and did not vaporize. As a result, those prior art compositions were not effective as an ultrasound contrast agents. Even though the boiling point of perfluoropentane is less than body temperature, Laplace surface tension effects prevented vaporization, and as a result the perfluoropentane remained as liquid nanodroplets in vivo.

Applicant has developed a perfluoropentane-based microbubble composition that is effective as an acoustic contrast agent, that forms a stable foam with a long shelf life, and that has a narrow distribution of bubble sizes. The microbubbles comprise a shell, formed from a stabilizing material, and a core containing a gas. In one embodiment, the microbubbles are formed by preparing a solution comprising a stabilizing material in a core gas environment (i.e., the gaseous environment contains only the type of gas that will fill the cores of the microbubbles), where a portion of the gas is also dissolved in the solution. The solution is shaken for a period of time to form a gas-filled microbubble foam.

In another embodiment, the gas environment comprises a partial pressure of a relatively insoluble gas and a partial pressure of a soluble gas, such as air, nitrogen, oxygen, or a combination thereof. In various embodiments, the partial pressure of the soluble gas is at or between about 20% to about 80% of ambient pressure. In one embodiment, the partial pressure of the soluble gas is about 35% of ambient pressure. In various embodiments, the relatively insoluble gas comprises a mixture of perfluoropentane and another fluorinated gas, such as without limitation perfluoropropane or perfluorobutane. In various embodiments, the relatively insoluble gas comprises a mixture of perfluoropentane and another fluorinated gas, wherein the partial pressure of the perfluoropentane is about 50% or more at ambient pressure.

In one embodiment, the microbubbles are formed by preparing a solution comprising a stabilizing material and a core gas material in the liquid state. The solution is homogenized and shaken to form a gas-filled microbubble foam.

By reference to "stabilizing material" Applicant means any material which can improve the stability of compositions containing the gases, gaseous precursors, liquids, targeting ligands and/or other bioactive agents described herein, including, for example, mixtures, suspensions, emulsions, dispersions, vesicles, microspheres or the like. Encompassed in the definition of "stabilizing material" are certain bioactive agents. The improved stability involves, for example, the maintenance of a relatively balanced condition, and may be exemplified, for example, by increased resistance of the composition against destruction, decomposition, degradation, and the like.

In certain embodiments, Applicant's composition comprises vesicles filled with gases, gaseous precursors, liquids, target ligands and/or bioactive agents, wherein the stabilizing compounds may serve to either form the vesicles or stabilize the vesicles, in either way serving to minimize or substantially (including completely) prevent the escape of gases, gaseous precursors and/or bioactive agents from the vesicles until release is desired. The term "substantially," as used in the context of preventing escape of gases, gaseous precursors and/or bioactive agents from the vesicles, means greater than about 50% is maintained entrapped in the vesicles until release is desired, and preferably greater than about 60%, more preferably greater than about 70%, even more preferably greater than about 80% or about 85%, still even more preferably greater than about 90% is maintained entrapped in the vesicles until release is desired. In some embodiments, greater than about 95% of the gases, gaseous precursors and/or bioactive agents are maintained entrapped until release is desired. The gases, gaseous precursors, liquids and/or bioactive agents may also be completely maintained entrapped (i.e., about 100% is maintained entrapped), until release is desired.

Exemplary stabilizing materials include, for example, lipids, proteins, polymers, carbohydrates and surfactants. The resulting mixture, suspension, emulsion or the like may comprise walls (i.e., films, membranes and the like) around the bioactive agent, gases and/or gaseous precursors, or may be substantially devoid of walls or membranes, if desired. The stabilizing may, if desired, form droplets. The stabilizing material may also comprise salts and/or sugars. In certain embodiments, the stabilizing materials may be substantially (including completely) cross-linked. The stabilizing material may be neutral, positively or negatively charged.

In one embodiment, the stabilizing material for preparing the microbubbles is a solution of PEG-Telomer-B ("PTB") sucrose. PEG-Telomer-B is a fluorosurfactant sold in commerce by DuPont. In one embodiment, the stabilizing material solution comprises a lipid suspension. In one embodiment, the lipid suspension comprises 2 mg of an 82 mole % dipalmitoylphosphatidylcholine ("DPPC"), Compound I,

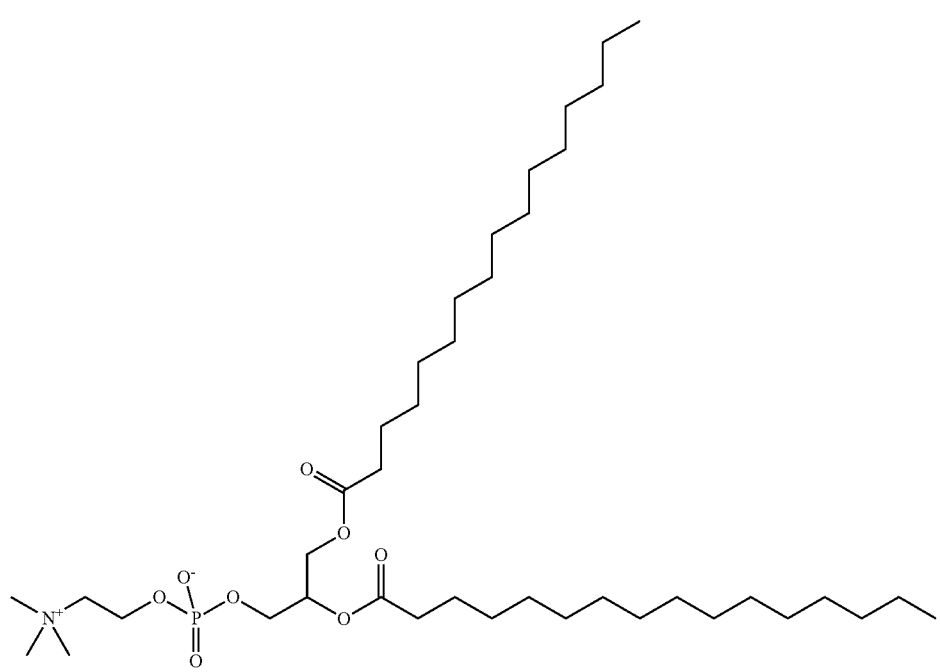

10 mole % dipalmitoylphosphatidylethanolaminepolyethylene glycol, Compound II, wherein n is adjusted such that Compound II comprises an average molecular weight of 5,000 daltons ("DPPE-PEG5000"),

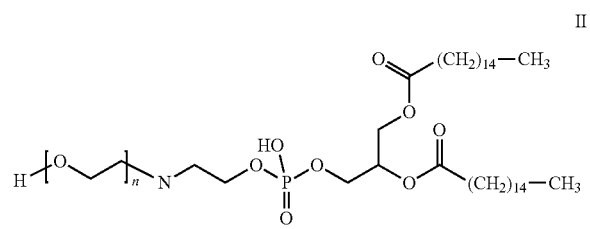

and 8 mole % dipalmitoylphosphatidic acid ("DPPA"), Compound III,

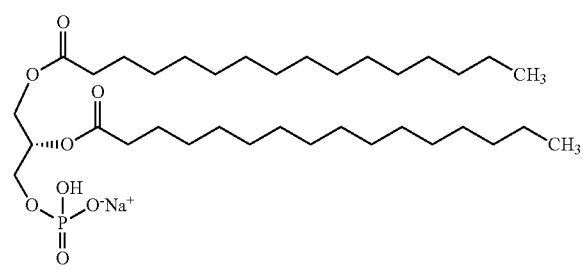

per 1 ml of a solution of saline/propylene glycol/glycerin solution.

In one embodiment, the lipid suspension may contain one or more bioconjugates, which comprise a targeting moiety attached to the PEG spacer on one of the lipids. In different embodiments, the bioconjugates comprise at or between about 0.1% to about 10% of the total lipid suspension.

In various embodiments, the stabilizing material comprises albumin, polylactide, polylactide-coglycolide, and other biocompatible polymers. In one embodiment, the stabilizing material comprises a fluorosurfactant. In one embodiment, the fluorosurfactant is polyethylene glycol-telomer-B, also known as PEG-Telomer B ("PTB"). In various embodiments, the fluorosurfactant is one of the fluorosurfactants described in U.S. Pat. Nos. 6,548,047, 5,276,146, 5,344,930, and 5,562,893, and U.S. application Ser. No. 08/465,868, filed Jun. 6, 1995, the disclosures of each of which are hereby incorporated by reference herein in their entirety.

In various embodiments, the stabilizing material comprises phospholipids, ceramides, sphingoglipids, cholesterol, or cholesterol derivatives. In one embodiment, the phospholipid chain length is at or between 10 to 24 carbon atoms in length and the acyl chain of the phospholipid at or between 16 to 18 carbons atoms in length. In some embodiments, the acyl chains are saturated and in others the acyl chains are unsaturated. In preferred embodiments, the stabilizing materials comprise phospholipids, including one or more of DPPC, DPPE, DPPA, DSPC, DSPE, DSPG and DAPC.

The choice of the stabilizing material used to form the microbubble shell varies on intended purpose. For example, in some embodiments, the stabilizing material results in a microbubble shell comprising targeting ligands or bioactive agents, which are particularity useful for therapeutic purposes.

The composition of the microbubble shell may be selected to decrease the reactivity of the microbubble with the surrounding material during circulation, thereby increasing the microbubbles useful life span. For example, in some embodiments, a portion of the lipids forming the bubble shell is PEGylated, with a PEG chain at or between a molecular weight of 1,000 to a molecular weight of 10,000.

In various embodiments, the percentage of PEGylated lipids relative to the total amount of lipids on a molar basis is at or between about 2% to about 20%. In various embodiments, the percentage of PEGylated lipids relative to the total amount of lipids is at or between 5 mole percent to about 15 mole percent.

A wide variety of lipids may be used as stabilizing materials and vesicles in the present invention. The lipids may be of either natural, synthetic or semi-synthetic origin, including for example, fatty acids, fluorinated lipids, neutral fats, phosphatides, oils, fluorinated oils, glycolipids, surface active agents (surfactants and fluorosurfactants), aliphatic alcohols, waxes, terpenes and steroids. Suitable lipids which may be used to prepare the stabilizing materials of the preset invention include, for example, fatty acids, lysolipids, fluorinated lipids, phosphocholines, such as those associated with platelet activation factors (PAF) (Avanti Polar Lipids, Alabaster, Ala.), including 1-alkyl-2-acetoyl-sn-glycero 3-phosphocholines, and 1-alkyl-2-hydroxy-sn-glycero 3-phosphocholines-which target blood clots; phosphatidylcholine with both saturated and unsaturated lipids, including dioleoylphosphatidylcholine; dimyristoyl-phosphatidylcholine; dipentadecanoylphosphatidylcholine; dilauroylphosphatdylcholine; dipalmitoylphosphatidylcholine (DPPC); distearoylphosphatidylcholine (DSPC); and diarachidonyl-phosphatidylcholine (DAPC); phosphatidylethanolamines, such as dioleoylphosphatidylethanolamine, dipalmitoyl-phosphatidylethanolamine (DPPE) and distearoyl-phosphatidylethanolamine (DSPE); phosphatidylserine; phosphatidylglycerols, including distearoylphosphatidylglycerol (DSPG); phosphatidylinositol; sphingolipids such as sphingomyelin; glycolipids such as ganglioside GM1 and GM2; glucolipids; sulfatides; glycosphingolipids; phosphatidic acids, such as dipalmitoylphosphatidic acid (DPPA) and distearoylphosphatidic acid (DSPA); palmitic acid; stearic acid; arachidonic acid; oleic acid; lipids bearing polymers, such as chitin, hyaluronic acid, polyvinylpyrrolidone or polyethylene glycol (PEG), also referred to herein as "pegylated lipids" with preferred lipid bearing polymers including DPPE-PEG ("DPPE-PEG"), which refers to the lipid DPPE having a PEG polymer attached thereto, including, for example, DPPE-PEG5000, which refers to DPPE having attached thereto a PEG polymer having a mean average molecular weight of about 5000.

In other embodiments, Applicant's stabilizing materials comprise lipids bearing sulfonated mono-, di-, oligo- or polysaccharides; cholesterol, cholesterol sulfate and cholesterol hemisuccinate; tocopherol hemisuccinate; lipids with ether and ester-linked fatty acids; polymerized lipids (a wide variety of which are well known in the art); diacetyl phosphate; dicetyl phosphate; stearylamine; cardiolipin; phospholipids with short chain fatty acids of about 6 to about 8 carbons in length; synthetic phospholipids with asymmetric acyl chains, such as, for example, one acyl chain of about 6 carbons and another acyl chain of about 12 carbons; ceramides; non-ionic liposomes including niosomes such as polyoxyalkylene (e.g., polyoxyethylene) fatty acid esters, polyoxyalkylene (e.g., polyoxyethylene) fatty alcohols, polyoxyalkylene (e.g., polyoxyethylene) fatty alcohol ethers, polyoxyalkylene (e.g., polyoxy-ethylene) sorbitan fatty acid esters (such as, for example, the class of compounds referred to as TWEEN, including, for example, TWEEN 20, TWEEN 40 and TWEEN 80, commercially available from ICI Americas, Inc., Wilmington, Del.).

In certain embodiments, Applicant's stabilizing materials comprise glycerol polyethylene glycol oxystearate, glycerol polyethylene glycol ricinoleate, alkyloxylated (e.g., ethoxylated) soybean sterols, alkyloxylated (e.g., ethoxylated) castor oil, polyoxyethylene-polyoxypropylene polymers, and polyoxyalkylene (e.g., polyoxyethylene) fatty acid stearates; sterol aliphatic acid esters including cholesterol sulfate, cholesterol butyrate, cholesterol isobutyrate, cholesterol palmitate, cholesterol stearate, lanosterol acetate, ergosterol palmitate, and phytosterol n-butyrate; sterol esters of sugar acids including cholesterol glucuronide, lanosterol glucuronide, 7-dehydro-cholesterol glucuronide, ergosterol glucuronide, cholesterol gluconate, lanosterol gluconate, and ergosterol gluconate; esters of sugar acids and alcohols including lauryl glucuronide, stearoyl glucuronide, myristoyl glucuronide, lauryl gluconate, myristoyl gluconate, and stearoyl gluconate; esters of sugars and aliphatic acids including sucrose laurate, fructose laurate, sucrose palmitate, sucrose stearate, glucuronic acid, gluconic acid and polyuronic acid; saponins including sarsasapogenin, smilagenin, hederagenin, oleanolic acid, and digitoxigenin; glycerol dilaurate, glycerol trilaurate, glycerol dipalmitate, glycerol and glycerol esters including glycerol tripalmitate, glycerol distearate, glycerol tristearate, glycerol dimyristate, glycerol trimyristate; long chain alcohols including n-decyl alcohol, lauryl alcohol, myristyl alcohol, cetyl alcohol, and n-octadecyl alcohol; 6-(5-cholesten-3.beta.-yloxy)-1-thio-.beta.-D-galactopyranoside; digalactosyldiglyceride; 6-(5-cholesten-3.beta.-yloxy)hexyl-6-deoxy-1-thio-.beta.-D-galacto-pyranoside; 6-(5-cholesten-3.beta.-yloxy)hexyl-6-amino-6-deoxyl-1-thio-.beta.-D-mannopyranoside; 12-(((7'-diethylaminocoumarin-3-yl)carbonyl)methylamino) octadecanoic acid; N-[12-(((7-diethylaminocoumarin-3-yl) carbonyl)methylamino)octadecanoyl]-2-aminopalmitic acid; cholesteryl(4'-trimethylammonio)butanoate; N-succinyldioleoylphosphatidylethanolamine; 1,2-dioleoyl-sn-glycerol; 1,2-dipalmitoyl-sn-3-succinylglycerol; 1,3-dipalmitoyl-2-succinylglycerol; 1-hexadecyl-2-palmitoylglycerophosphoethanolamine and palmitoylhomocysteine, and/or any combinations thereof.

In the case of stabilizing materials which contain both cationic and non-cationic lipids, a wide variety of lipids, as described above, may be employed as the non-cationic lipid. Preferably, the non-cationic lipid comprises one or more of DPPC, DPPE and dioleoylphosphatidylethanolamine. In lieu of the cationic lipids listed above, lipids bearing cationic polymers, such as polylysine or polyarginine, as well as alkyl phosphonates, alkyl phosphinates, and alkyl phosphites, may also be used in the stabilizing materials.

Saturated and unsaturated fatty acids which may be employed in the present stabilizing materials include molecules that preferably contain from about 12 carbon atoms to about 22 carbon atoms, in linear or branched form. Hydrocarbon groups consisting of isoprenoid units and/or prenyl groups can be used. Suitable saturated fatty acids include, for example, lauric, myristic, palmitic, and stearic acids. Suitable unsaturated fatty acids include, for example, lauroleic, physeteric, myristoleic, palmitoleic, petroselinic, and oleic acids. Suitable branched fatty acids include, for example, isolauric, isomyristic, isopalmitic, and isostearic acids.

Other useful lipids or combinations thereof apparent to one skilled in the art which are in keeping with the spirit of the present invention are also encompassed by the present invention. For example, carbohydrate-bearing lipids may be employed, as described in U.S. Pat. No. 4,310,505, the disclosure of which is hereby incorporated herein by reference in its entirety.

In addition to stabilizing materials and/or vesicles formulated from lipids, embodiments of the present invention may involve vesicles formulated, in whole or in part, from proteins or derivatives thereof. Suitable proteins for use in the present invention include, for example, albumin, hemoglobin, .alpha.-1-antitrypsin, .alpha.-fetoprotein aminotransferases, amylase, C-reactive protein, carcinoembryonic antigen, ceruloplasmin, complement, creatine phosphokinase, ferritin, fibrinogen, fibrin, transpeptidase, gastrin, serum globulins, myoglobin, immunoglobulins, lactate dehydrogenase, lipase, lipoproteins, acid phosphatase, alkaline phosphatase, .alpha.-1-serum protein fraction, .alpha.-2-serum protein fraction, .beta.-protein fraction, .gamma.-protein fraction and .gamma.-glutamyl transferase. Other stabilizing materials and vesicles formulated from proteins that may be used in the present invention are described, for example, in U.S. Pat. Nos. 4,572,203, 4,718,433, 4,774,958, and 4,957,656, the disclosures of which are hereby incorporated herein by reference in their entirety. Other protein-based stabilizing materials and vesicles, in addition to those described above and in the aforementioned patents, would be apparent to one of ordinary skill in the art in view of the present disclosure.

In addition to stabilizing materials and/or vesicles formulated from lipids and/or proteins, embodiments of the present invention may also involve stabilizing materials or vesicles formulated from polymers which may be of natural, semi-synthetic (modified natural) or synthetic origin. Polymer denotes a compound comprised of two or more repeating monomeric units, and preferably 10 or more ring monomeric units. Semi-synthetic polymer (or modified natural polymer) denotes a natural polymer that has been chemically modified in some fashion. Suitable natural polymers include naturally occurring polysaccharides, such as, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthin gum, starch and various other natural homopolymer or heteropolymers, such as those containing one or more of the following aldoses, ketoses, acids or amines: erythrose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof. Accordingly, suitable polymers include, for example, proteins, such as albumin.

Exemplary semi-synthetic polymers include carboxymethylcellulose, hydroxymethylcellulose, hydroxypropylmethylcellulose, methyl-cellulose, and methoxycellulose. Exemplary synthetic polymers suitable for use in the present invention include polyphosphazenes, polyalkylenes (e.g., polyethylene), such as, for example, polyethylene glycol (including, for example, the class of compounds referred to as Pluronics, commercially available from BASF, Parsippany, N.J.), polyoxyalkylenes (e.g., polyoxyethylene), and polyethylene terephthlate, polypropylenes (such as, for example, polypropylene glycol), polyurethanes (such as, for example, polyvinyl alcohol (PVA), polyvinyl chloride and polyvinylpyrrolidone), polyamides including nylon, polystyrene, polylactic acids, fluorinated hydrocarbon polymers, fluorinated carbon polymers (such as, for example, polytetrafluoro-ethylene), acrylate, methacrylate, and polymethylmethacrylate, and derivatives thereof. Preferred are synthetic polymers or copolymers prepared from monomers, such as acrylic acid, methacrylic acid, ethyleneimine, crotonic acid, acrylamide, ethyl acrylate, methyl methacrylate, 2-hydroxyethyl methacrylate (HEMA), lactic acid, glycolic acid, epsilon-caprolactone, acrolein, cyanoacrylate, bisphenol A, epichlorhydin, hydroxyalkyl-acrylates, siloxane, dimethylsiloxane, ethylene oxide, ethylene glycol, hydroxyalkyl-methacrylates, N-substituted acrylamides, N-substituted methacrylamides, N-vinyl-2-pyrrolidone, 2,4-pentadiene-1-ol, vinyl acetate, acrylonitrile, styrene, p-amino-styene, p-amino-benzyl-styrene, sodium styrene sulfonate, sodium 2-sulfoxyethyl-methacrylate, vinyl pyridine, aminoethyl methacrylates, 2-methacryl-oyloxytrimethylammonium chloride, and polyvinylidene, as well polyfunctional crosslinking monomers such as N,N'-methylenebisacrylamide, ethylene glycol dimethacrylates, 2,2'-(p-phenylenedioxy)diethyl dimethacrylate, divinylbenzene, triallylamine and methylenebis(4-phenylisocyanate), including combinations thereof. Preferable polymers include polyacrylic acid, polyethyleneimine, polymethacrylic acid, polymethylmethcrylate, polysiloxane, polydimethylsiloxane, polylactic acid, poly(epsilon-caprolactone), epoxy resin, poly(ethylene oxide), poly(ethylene glycol), and polyamide (nylon) polymers.

Preferable copolymers include the following: polyvinylidene-polyacrylonitrile, polyvinylidene-polyacrylonitrile-polymethyl-methacrylate, polystyrene-polyacrylonitrile and poly d-l, lactide co-glycolide polymers. A preferred copolymer is polyvinylidene-polyacrylonitrile. Other suitable monomers and polymers will be apparent to one skilled in the art in view of the present disclosure.

Stabilizing materials and vesicles may be prepared from other materials. The materials may be basic and fundamental, and may form the primary basis for creating or establishing the stabilized materials, such as gas and gaseous precursor filled vesicles. For example, surfactants and fluorosurfactants may be basic and fundamental materials for preparing stabilizing materials and vesicles. On the other hand, the materials may be auxiliary, and act as subsidiary or supplementary agents which may enhance the functioning of the basic stabilizing material(s), or contribute some desired property in addition to that afforded by the basic stabilizing material(s).

Fluorine can be introduced into any of the aforementioned stabilizing materials or vesicles either in their monomeric or polymeric form. Preferably, fluorine moieties are introduced into monomers, such as fatty acids, amino acids or polymerizable synthetic organic compounds, which are then polymerized for subsequent use as stabilizing materials and/or vesicles.

The introduction of fluorine into stabilizing materials and/or vesicles may also be accomplished by forming vesicles in the presence of a perfluorocarbon gas. For example, when vesicles are formed from proteins, such as human serum albumin in the presence of a perfluorocarbon gas, such as perfluoropropane, using mechanical cavitation, fluorine from the gas phase becomes bound to the protein vesicles during formation. The presence of fluorine in the vesicles and/or stabilizing materials can be detected by NMR of vesicle debris which has been purified from disrupted vesicles. Fluorine can also be introduced into stabilizing materials and/or vesicles using other methods, such as sonication, spray-drying or emulsification techniques.

Another way in which fluorine can be introduced into the stabilizing material and/or vesicle is by using a fluorine-containing reactive compound. The term "reactive compound" refers to compounds which are capable of interacting with the stabilizing material and/or vesicle in such a manner that fluorine moieties become covalently attached to the stabilizing material and/or vesicle. When the stabilizing material is a protein, preferred reactive compounds are either alkyl esters or acyl halides which are capable of reacting with the protein's amino groups to form an amide linkage via an acylation reaction. The reactive compound can be introduced at any stage during vesicle formation, but is preferably added to the gas phase prior to vesicle formation. For example, when vesicles are to be made using mechanical or ultrasound cavitation techniques, the reactive compound can be added to the gas phase by bubbling the gas to be used in the formation of the vesicles (starting gas) through a solution of the reactive compound into the gas phase. The resultant gas mixture, which now contains the starting gas and the reactive compound, is then used to form vesicles. The vesicles are preferably formed by sonication of human serum albumin in the presence of a gas mixture, as described in U.S. Pat. No. 4,957,656, the disclosure of which is hereby incorporated herein by reference in its entirety.

Suitable fluorine containing alkyl esters and acyl halides for use as stabilizing materials and/or vesicle forming materials in the present invention include, for example, diethyl hexafluoroglutarate, diethyl tetrafluorosuccinate, methyl heptafluorobutyrate, ethyl heptafluorobutyrate, ethyl pentafluoropropionate, methyl pentafluoropropionate, ethyl perfluorooctanoate, methyl perfluorooctanoate, nonafluoropentanoyl chloride, perfluoro-propionyl chloride, hexafluoroglutaryl chloride and heptafluorobutyryl chloride.

Other fluorine containing reactive compounds can also be synthesized and used as the stabilizing materials and/or vesicle forming materials in the present invention, including, for example, aldehydes, isocyanates, isothiocyanates, epoxides, sulfonyl halides, anhydrides, acid halides and alkyl sulfonates, which contain perfluorocarbon moieties, including —$CF_3$, —$C_2F_5$, —$C_3F_4$ and —$C(CF_3)_3$. These reactive compounds can be used to introduce fluorine moieties into any of the aforementioned stabilizing materials by choosing a combination which is appropriate to achieve covalent attachment of the fluorine moiety.

Sufficient fluorine should be introduced to decrease the permeability of the vesicle to the aqueous environment. This will result in a slower rate of gas exchange with the aqueous environment which is evidenced by enhanced pressure resistance. Although the specific amount of fluorine necessary to stabilize the vesicle will depend on the components of the vesicle and the gas contained therein, after introduction of fluorine the vesicle will preferably contain 0.01 to 20% by weight, and more preferably about 1 to 10% by weight fluorine.

It may be desirable to use a fluorinated liquid, especially a liquid perfluorocarbon or a liquid perfluoroether, which are liquids at the temperature of use, including, for example, the in vivo temperature of the human body, to assist or enhance the stability of the gaseous precursor filled compositions of the present invention. Suitable liquid perfluorocarbons and liquid perfluoroethers include, for example, perfluoroheptane, perfluorooctane, perfluorononane, perfluorodecane, perfluorodecalin, perfluorododecalin, perfluorooctyliodide, perfluorooctylbromide, perfluorotripropylamine, perfluorotributylamine, perfluorobutylethyl ether, bis(perfluoroisopropyl)ether and bis(perfluoropropyl)ether. Among these, perfluorooctylbromide is preferred. Although not intending to be bound by any theory of operation, in the case of vesicle compositions, the fluorinated liquid compound may be situated at the interface between the gas and the membrane or wall surface of the vesicle. Thus, an additional stabilizing layer of fluorinated liquid compound may be formed on the internal surface of the stabilizing composition, and this fluorinated liquid compound layer may also prevent the gas from diffusing through the vesicle membrane.

Preferred surfactants which may also be used in the compositions of the present invention are partially fluorinated phosphocholine surfactants. In these preferred fluorinated surfactants, the dual alkyl compounds may be fluorinated at the terminal alkyl chains and the proximal carbons may be hydrogenated. These fluorinated phosphocholine surfactants may be used for making the stabilizing materials and/or vesicles of the present invention.

Preferred embodiments of the present invention involve vesicles which comprise three components: (1) a neutral lipid, for example, a nonionic or zwitterionic lipid, (2) a negatively charged lipid, and (3) a lipid bearing a stabilizing material, for example, a hydrophilic polymer. Preferably, the amount of the negatively charged lipid will be greater than about 1 mole percent of the total lipid present, and the amount of lipid bearing a hydrophilic polymer will be greater than about 1 mole percent of the total lipid present. Exemplary and preferred negatively charged lipids include phosphatidic acids. The lipid bearing a hydrophilic polymer will desirably be a lipid covalently linked to the polymer, and the polymer will preferably have a weight average molecular weight of from about 400 to about 100,000. Suitable hydrophilic polymers are preferably selected from the group consisting of polyethylene glycol (PEG), polypropylene glycol, polyvinyl alcohol, and polyvinyl pyrrolidone and copolymers thereof, with PEG polymers being preferred. Preferably, the PEG polymer has a molecular weight of from about 1000 to about 7500, with molecular weights of from about 1000 to about 5000 being more preferred. The PEG or other polymer may be bound to the lipid, for example, DPPE, through a covalent bond, such as an amide, carbamate or amine linkage. In addition, the PEG or other polymer may be linked to a targeting ligand, or other phospholipids, with a covalent bond including, for example, amide, ester, ether, thioester, thioamide or disulfide bonds. Where the hydrophilic polymer is PEG, a lipid bearing such a polymer will be said to be "pegylated." In preferred form, the lipid bearing a hydrophilic polymer may be DPPE-PEG, including, for example, DPPE-PEG5000, which refers to DPPE having a polyethylene glycol polymer of a mean weight average molecular weight of about 5000 attached thereto (DPPE-PEG5000). Another suitable pegylated lipid is distearoylphosphatidylethanol-amine-polyethylene glycol 5000 (DSPE-PEG5000).

In preferred embodiments of the present invention, the lipid compositions may include about 77.5 mole % DPPC, 12.5 mole % of DPPA, and 10 mole % of DPPE-PEG5000. Also preferred are compositions which comprise about 80 to about 90 mole % DPPC, about 5 to about 15 mole % DPPA and about 5 to about 15 mole % DPPE-PEG5000. Especially preferred are compositions which comprise DPPC, DPPA and DPPE-PEG5000 in a mole % ratio of 82:10:8, respectively. DPPC is substantially neutral, since the phosphatidyl portion is negatively charged and the choline portion is positively charged. Consequently, DPPA, which is negatively charged, may be added to enhance stabilization in accordance with the mechanism described above. DPPE-PEG provides a pegylated material bound to the lipid membrane or skin of the vesicle by the DPPE moiety, with the PEG moiety free to surround the vesicle membrane or skin, and thereby form a physical barrier to various enzymatic and other endogenous agents in the body whose function is to degrade such foreign materials. The DPPE-PEG may provide more vesicles of a smaller size which are safe and stable to pressure when combined with other lipids, such as DPPC and DPPA, in the given ratios. It is also theorized that the pegylated material, because of its structural similarity to water, may be able to defeat the action of the macrophages of the human immune system, which would otherwise tend to surround and remove the foreign object. The result is an increase in the time during which the stabilized vesicles may function as diagnostic imaging contrast media.

In one embodiment, the lipid compositions comprise about 95 mole percent of DPPC with about 5 mole percent DPPE-PEG-2000 and about 95 mole percent of DSPC with about 5 mole percent DSPE-PEG-2000.

In various embodiments, the microbubble core gas is nitrogen, oxygen, sulfur hexafluoride, perfluoropropane, perfluorobutane, perfluoropentane, or perfluorohexane. For the purposes of imaging and drug delivery, the ideal microbubble core gas has low aqueous solubility coupled with a boiling point below body temperature. This results in a microbubble with a long circulation time, a long useful life span, and high echogenic qualities.

Applicant's gaseous precursors include, for example, fluorinated carbons, perfluorocarbons, sulfur hexafluoride, perfluoro ethers and combinations thereof. As the stilled artisan will appreciate, a particular fluorinated compound, such as sulfur hexafluoride, a perfluorocarbon or a perfluoro ether, may exist in the liquid state when the compositions are first made, and are thus used as a gaseous precursor. Whether the fluorinated compound is a liquid generally depends on its liquid/gas phase transition temperature, or boiling point. For example, a preferred perfluorocarbon, perfluoropentane, has a liquid/gas phase transition temperature (boiling point) of 29.5° C. This means that perfluoropentane is generally a liquid at room temperature (about 25° C.), but is converted to a gas within the human body, the normal temperature of which is about 37° C., which is above the transition temperature of perfluoropentane. Thus, under normal circumstances, perfluoropentane is a gaseous precursor. As known to one skilled in the art, the effective boiling point of a substance may be related to the pressure to which that substance is exposed. This relationship is exemplified by the ideal gas law: $PV=nRT$, where P is pressure, V is volume, n is moles of substance, R is the gas constant, and T is temperature. The ideal gas law indicates that as pressure increases, the effective boiling point also increases. Conversely, as pressure decreases, the effective boiling point decreases.

Fluorocarbons for use as gaseous precursors in the compositions of the present invention include partially or fully fluorinated carbons, preferably perfluorocarbons that are saturated, unsaturated or cyclic. The preferred perfluorocarbons include, for example, perfluoromethane, perfluoroethane, perfluoropropane, perfluorocyclopropane, perfluorobutane, perfluorocyclobutane, perfluoropentane, perfluorocyclopentane, perfluorohexane, perfluorocyclohexane, and mixtures thereof. More preferably, the perfluorocarbon is perfluorohexane, perfluoropentane, perfluoropropane or perfluorobutane.

Preferred ethers include partially or fully fluorinated ethers, preferably perfluorinated ethers having a boiling point of from about 36° C. to about 60° C. Fluorinated ethers are ethers in which one or more hydrogen atoms is replaced by a fluorine atom. Preferred perfluorinated ethers for use as gaseous precursors in the present invention include, for example, perfluorotetrahydropyran, perfluoromethyltetrahydrofuran, perfluorobutylmethyl ether (e.g., perfluoro t-butylmethyl ether, perfluoro isobutyl methyl ether, perfluoro n-butyl methyl ether), perfluoropropylethyl ether (e.g., perfluoro isopropyl ethyl ether, perfluoro n-propyl ethyl ether), perfluorocyclobutylmethyl ether, perfluorocyclopropylethyl ether, perfluoropropylmethyl ether (e.g., perfluoro isopropyl methyl ether, perfluoro n-propyl methyl ether), perfluorodiethyl ether, perfluorocyclopropylmethyl ether, perfluoromethylethyl ether and perfluorodimethyl ether.

Other preferred perfluoroether analogues contain between 4 and 6 carbon atoms, and optionally contain one halide ion, preferably BC. For example, compounds having the structure $C_nF_yH_xOBr$, where n is an integer of from 1 to about 6, y is an integer of from 0 to about 13, and x is an integer of from 0 to about 13, are useful as gaseous precursors.

Other preferable fluorinated compounds for use as gaseous precursors in the present invention are sulfur hexafluoride and heptafluoropropane, including 1,1,1,2,3,3,3-heptafluoropropane and its isomer, 1,1,2,2,3,3,3-heptafluoropropane. Mixtures of different types of compounds, such as mixtures of a fluorinated compound (e.g., a perfluorocarbon or a perfluoroether) and another type of gas or gaseous precursor can also be used in the compositions of the present invention. Other gases and gaseous precursors are well known to one skilled in the art.

Generally, preferred gaseous precursors undergo phase transition to gas at a temperature up to about 57° C., preferably from about 20° C. to about 52° C., preferably from about 37° C., to about 50° C., more preferably from about 38° C. to about 48° C., even more preferably from about 38° C. to about 46° C., still even more preferably from about 38° C. to about 44° C., even still more preferably from about 38° C., to about 42° C. Most preferably, the gaseous precursors undergo a phase transition at a temperature of about less than 40° C. As will be recognized by one skilled in the art, the optimal phase transition temperature of a gaseous precursor for use in a particular application will depend upon considerations such as, for example, the particular patient, the tissue being targeted, the nature of the physiological stress state (i.e., disease, infection or inflammation, etc.) causing the increased temperature, the stabilizing material used, and/or the bioactive agent to be delivered.

Additionally, one skilled in the art will recognize that the phase transition temperature of a compound may be affected by local conditions within the tissue, such as, for example, local pressure (for example, interstitial, interfacial, or other pressures in the region). By way of example, if the pressure within the tissues is higher than ambient pressure, this will be expected to raise the phase transition temperature. The extent of such effects may be estimated using standard gas law predictions, such as Charles' Law and Boyle's Law. As an approximation, compounds having a liquid-to-gas phase transition temperature between about 30° C. and about 50° C. can be expected to exhibit about a 1° C. increase in the phase transition temperature for every 25 mm Hg increase in pressure. For example, the liquid-to-gas phase transition temperature (boiling point) of perfluoropentane is 29.5° C. at a standard pressure of about 760 mm Hg, but the boiling point is about 30.5. ° C. at an interstitial pressure of 795 mm Hg.

Materials used in stabilizing the gaseous precursor, discussed herein, may also affect the phase transition temperature of the gaseous precursor. In general, the stabilizing material is expected to increase the phase transition temperature of the gaseous precursor. In particular, a relatively rigid polymeric material, such as, for example, polycyanomethacrylate, may have a significant effect on the phase transition temperature of the gaseous precursor. Such an effect must be considered in the selection of the gaseous precursor and the stabilizing material.

The gaseous precursors and/or gases are preferably incorporated in the stabilizing materials and/or vesicles irrespective of the physical nature of the composition. Thus, it is contemplated that the gaseous precursors and/or gases may be incorporated, for example, in stabilizing materials in which the stabilizing materials are aggregated randomly, such as emulsions, dispersions or suspensions, as well as in vesicles, including vesicles which are formulated from lipids, such as micelles and liposomes. Incorporation of the gases and/or gaseous precursors in the stabilizing materials and/or vesicles may be achieved by using any of a number of methods.

The terms "stable" or "stabilized" mean that the vesicles may be substantially resistant to degradation, including, for example, loss of vesicle structure or encapsulated gas, gaseous precursor and/or bioactive agent, for a useful period of time. Typically, the vesicles employed in the present invention have a desirable shelf life, often retaining at least about 90% by volume of its original structure for a period of at least about two to three weeks under normal ambient conditions. In preferred form, the vesicles are desirably stable for a period of time of at least about 1 month, more preferably at least about 2 months, even more preferably at least about 6 months, still more preferably about eighteen months, and yet more preferably up to about 3 years. The vesicles described herein, including gas and/or gaseous precursor filled vesicles, may also be stable even under adverse conditions, such as temperatures and pressures which are above or below those experienced under normal ambient conditions.

The gas and/or gaseous precursor filled vesicles used in the present invention may be controlled according to size, solubility and heat stability by choosing from among the various additional or auxiliary stabilizing materials described herein. These materials can affect the parameters of the vesicles, especially vesicles formulated from lipids, not only by their physical interaction with the membranes, but also by their ability to modify the viscosity and surface tension of the surface of the gas and/or gaseous precursor filled vesicle. Accordingly, the gas and/or gaseous precursor filled vesicles used in the present invention may be favorably modified and further stabilized, for example, by the addition of one or more of a wide variety of (i) viscosity modifiers, including, for example, carbohydrates and their phosphorylated and sulfonated derivatives; polyethers, preferably with molecular weight ranges between 400 and 100,000; and di- and trihydroxy alkanes and their polymers, preferably with molecular weight ranges between 200 and 50,000; (ii) emulsifying and/or solubilizing agents including, for example, acacia, cholesterol, diethanolamine, glyceryl monostearate, lanolin alcohols, lecithin, mono- and di-glycerides, mono-ethanolamine, oleic acid, oleyl alcohol, poloxamer, for example, poloxamer 188, poloxamer 184, poloxamer 181, PLURONICS (BASF, Parsippany, N.J.), polyoxyethylene 50 stearate, polyoxyl 35 castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfite, sodium stearate, sorbitan mono-laurate, sorbitan mono-oleate, sorbitan mono-palmitate, sorbitan monostearate, stearic acid, trolamine, and emulsifying wax; (iii) suspending and/or viscosity-increasing agents, including, for example, acacia, agar, alginic acid, aluminum mono-stearate, bentonite, magma, carbomer 934P, carboxymethyl-cellulose, calcium and sodium and sodium 12, carrageenan, hyaluronic acid, cellulose, dextran, gelatin, guar gum, locust bean gum, veegum, hydroxyethyl cellulose, hydroxypropyl methyl-cellulose, magnesium-aluminum-silicate, ZEOLITES, methylcellulose, pectin, polyethylene oxide, povidone, propylene glycol alginate, silicon dioxide, sodium alginate, tragacanth, xanthan gum, .alpha.-d-gluconolactone, glycerol and mannitol; (iv) synthetic suspending agents, such as polyethylene glycol (PEG), polyvinylpyrrolidone (PVP), polyvinylalcohol (PVA), polypropylene glycol (PPG), and polysorbate; and (v) tonicity raising agents which stabilize and add tonicity, including, for example, sorbitol, mannitol, trehalose, sucrose, propylene glycol and glycerol.

The present stabilizing materials and/or vesicles are desirably formulated in an aqueous environment which can induce the stabilizing material (e.g., a lipid, because of its hydrophobic-hydrophilic nature) to form vesicles, which may be the most stable configuration which can be achieved in such an environment. The diluents which can be employed to create such an aqueous environment include, for example, water, including deionized water, normal saline, physiological saline, or water containing one or more dissolved solutes, such as salts or sugars. Accordingly, when reference is made to heating the gaseous precursor filled compositions prior to administration to a patient, such heating preferably includes heating the aqueous environment or milieu in which the gaseous precursor filled compositions are contained.

The following Examples are presented to further illustrate to persons skilled in the art how to make and use the invention. These Examples are not intended as a limitation, however, upon the scope of Applicant's invention.

Example 1

Perfluoropentane Gas Filled Microbubbles with a PTB Shell Formed in an Atmosphere of Perfluoropentane The headspace of a 4 mL vial is determined by first filling the vial with water. A septum and cap is added to the vial to displace enough water to allow the vial to be sealed. The septum and cap are then removed. The volume of water remaining in the vial, representing the precise volume of the vial, is then emptied into a graduated cylinder, measured and the amount recorded.

The headspace volume of the vial is determined by subtracting a desired volume of a stabilizing material from the measured volume of the vial recorded in the previous step. The amount of core gas that would fill the headspace volume when volatilized is then determined using Ideal Gas Law calculations.

Next, 3 mL of a PTB/sucrose solution, the stabilizing material, is added to the vial. A septum is placed onto the vial, and the vial is capped and crimped. The headspace of the vial is evacuated using a 21 gauge needle inserted through the septa and vacuumed for 20 minutes at 400 Torr.

The vial is placed in a freezer until the temperature of the solution is approximately 4° C. The vial is removed from the freezer and placed on an analytical balance. The balance is tared to 0 and 0.0130 grams of perfluoropentane (the amount derived from the headspace volume measurement) is added using a frozen, gas tight, syringe. The vial is exposed to room temperature for approximately 20 minutes after the solution has fully melted. The headspace is again evacuated using the 21 gauge needle inserted through the septa at 400 Torr until the perfluoropentane, initially visible as a liquid at the bottom of the vial, is fully volatized. The vial is placed on a mechanical shaker (Bristol-Myers Vialmix) set at 75 Hz for 45 seconds. The composition of Example 1 comprising a PTB/sucrose stabilizing material is designated as Composition 140 in FIG. 1.

Example 2

Perfluoropentane Gas Filled Microbubbles with a Lipid Shell Formed in an Atmosphere of Perfluoropentane The method in Example 1 is followed, except that 3 mL of a lipid suspension is used as the stabilizing material in place of the PTB/sucrose solution. The lipid suspension comprises 2 mg of an 82 mole % dipalmitoylphosphatidylcholine ("DPPC"), 10 mole % dipalmitoylphosphatidylethanolaminepolyethylene glycol having an average molecular weight of 5,000 daltons ("DPPE-PEG5000"), and 8 mole % dipalmitoylphosphatidic acid ("DPPA") mixture per 1 ml of a solution of saline/propylene glycol/glycerin solution. The composition of Example 2 comprising DPPC/DPPE-PEG 5000/DPPA stabilizing material is designated as Composition 120 in FIG. 1.

Example 3

Perfluoropentane Gas Filled Microbubbles with a PTB Shell Formed in Solution

Approximately 30 mL of a PTB/sucrose solution is prepared. The solution is placed in a round bottom flask containing a stir bar. A nitrogen manifold is attached to the flask. Perfluoropentane was added to the flask. The nitrogen manifold is opened to pressurize the flask with nitrogen gas. The flask is placed on a stir plate and stirred for approximately 60 minutes. The contents of the flask are added to a homogenizer and allowed to circulate for 6 cycles, which is determined by the homogenizer flow rate and volume of mixture. The mixture is removed from the homogenizer and filtered through a 0.2 micron sterile filter.

Approximately 3 mL of the filtered mixture is dispensed into a clean, sterile, nitrogen evacuated 7 mL serum vial. A septum is immediately added to the vial and the vial is capped and crimped. The vial is placed on a mechanical shaker (Bristol-Myers Vialmix) set at about 75 Hz rpm for about 45 seconds. The composition of Example 3 comprising a PTB/sucrose stabilizing material is designated as Composition 150 in FIG. 1.

Example 4

Perfluoropentane Gas Filled Microbubbles with a Lipid Shell Formed in Solution

The method in Example 3 was followed, with the exception that 3 mL of a lipid suspension is used as the stabilizing material in place of the PTB/sucrose solution. The lipid suspension comprised 2 mg of an 82 mole % dipalmitoylphosphatidylcholine ("DPPC"), 10 mole % dipalmitoylphosphatidylethanolaminepolyethylene glycol having an average molecular weight of 5,000 daltons ("DPPE-PEG5000"), and 8 mole % dipalmitoylphosphatidic acid ("DPPA") mixture per 1 ml of a solution of saline/propylene glycol/glycerin solution. The composition of Example 4 comprising DPPC/DPPE-PEG 5000/DPPA stabilizing material is designated as Composition 130 in FIG. 1.

Example 5

Perfluoropentane Gas Filled Microbubbles with a Lipid Shell Formed in an Environment of Perfluoropentane Gas A stabilizing material is prepared by combining 90 mole % dipalmitoylphosphatidylcholine ("DPPC"), a phospholipid, and 10 mole % DPPE-PEG5000. Alternately DPPE-PEG2000, which is dipalmitoylphosphatidylethanolaminepolyethylene glycol having an average molecular weight of 2,000 daltons, may be substituted for the DPPE-PEG5000.

A solution is prepared from phosphate buffered saline, propylene glycol, and glycerol at an 8:1:1 volume ratio. Phosphate buffered saline ("PBS") is an aqueous salt solution that helps to maintain a constant pH, yet is non-toxic to cells. The DPPC/DPPE mixture is added to the solution at a concentration of 2.5 mg per mL of solution to create a lipid suspension.

Perfluoropentane is blended into the lipid suspension under pressure at low temperature (about 4° C.). The perfluoropentane is added at a concentration of 25 mg per mL of the lipid suspension. The perfluoropentane/lipid suspension is homogenized with a high pressure homogenizer, such as a MICROFLUIDIZER from Microfluidics. After homogenization, 1 mL of the perfluoropentane/lipid suspension is added to a 3 mL serum vial.

The vial is chilled until the contents reach about 4° C. The headspace is then evacuated under pressure and the vial sealed. In one embodiment, the vial is evacuated and sealed using a Bosch automated filling and sealing device. The sealed vial is shaken for 45 seconds on a mechanical shaker at about 75 Hz yielding a microbubble product suitable for injection.

Example 6

A suspension of phospholipids DPPC (90 mole percent) and DPPE-PEG5000 and/or DPPE-PEG2000 (10 mole percent) is prepared as a suspension of the lipids in phosphate buffered normal saline PBS and propylene glycol and glycerol, 8:1:1, at a lipid concentration of 2.5 mg per ml. DDFP is blended into the lipid suspension under pressure and low temperature (e.g. 4 degrees centigrade) and homogenized with a high pressure homogenizer. The concentration of DDFP in the final suspension is 25 mg/ml. The material is introduced into 3 ml glass vials at a fill volume of 1 ml of the DDFP/lipid suspension. The material is chilled to 4 degrees C. and the headspace evacuated under reduced pressure and the vials sealed. The sealed vial is shaken for 45 seconds on a mechanical shaker at about 75 Hz yielding a microbubble product suitable for injection.

Example 7

Example 6 is substantially repeated except that the headspace of the vial is rapidly evacuated and sealed using a Bosch automated filling and sealing device.

Example 8

Example 7 is substantially repeated except that a tank is fitted to the Bosch automated filling unit. The unit volatizes the DDFP gas and injects a precise quantity of volatilized gas into each vial. Note that a second tank could be equipped to inject other gases such as air, nitrogen or oxygen. The gases could also be premixed to ratios ranging from about 80%/20% ambient pressure soluble gas/DDFP to about 20%/80% ambient pressure soluble gas/DDFP.

Example 9

Examples 7 and 8 are substantially repeated except that rather than 25 mg per ml of DDFP, the concentration of DDFP is 16.25 mg per ml in the lipid suspension. A fill volume of 1 ml is entered into the vials. Using the Bosch device the headspace is evacuated and air is filled into the headspace at 0.35 ambient atmospheric pressure. The vials are crimped and sealed and shaken as above. The product yields gas filled microbubbles of about 0.35 air and about 0.65 DDFP.

Example 10

Lipid coated perfluoropropane and perfluoropentane microbubbles are compared for echocardiography. Both of the agents give robust ventricular enhancement. The degree of enhancement of visualization of myocardial blood flow is superior with the perfluoropentane-based agent. The perfluoropentane-based agent is more resistant to higher acoustic pressures which makes it easier to assess the myocardial blood flow.

Example 11

Targeted lipid coated perfluoropropane and perfluoropentane microbubbles are prepared with 10 mole percent DPPE-PEG 2000-fibrin binding peptide. In vitro sonothrombolysis is performed on human clot. The perfluoropentane based MB give better imaging contrast for detection of clot and a higher rate of clot lysis.

Effectiveness of Applicant's Microbubble Compositions

Applicant's microbubble compositions, prepared consistent with the steps described in the Examples above, yield a large number of bubbles, exhibit a long shelf life, and displays a narrow bubble size distribution.

Referring to FIG. 1, chart 100 graphically illustrates the quality of bubbles remaining over time for a number of different bubbles compositions and preparation methods. The x-axis 112 represents time (in hours) and the y-axis 110 represents the height of foam present in the vial (in millimeters).

Curve 120 shows the amount of microbubbles as a function of time, where those microbubbles were formed using the composition and method of Example 2. The resulting microbubbles have a lipid shell with a core comprising perfluoropentane gas.

Curve 130 shows the amount of microbubbles as a function of time, where those microbubbles were formed using the composition and method of Example 4 above (i.e., bubbles formed in the lipid suspension). The resulting microbubbles have a lipid shell with a core containing perfluoropentane.

Curve 140 shows the amount of microbubbles as a function of time, where those microbubbles were formed using the composition and method of Example 1. The resulting microbubbles have a PTB shell with a core comprising perfluoropentane gas.

Curve 150 shows the amount of microbubbles as a function of time, where those microbubbles were formed using the composition and method of Example 3. The resulting microbubbles have a PTB shell with a core comprising perfluoropentane gas.

Microbubble compositions formed from the lipid suspension (curves 120 and 130) have, in general, more bubbles (measured in terms of foam height) than those compositions formed from the PTB solution (curves 140 and 150). In addition, the microbubbles formed in head space comprising perfluoropentane gas, represented by lines curves 120 and 130, are more stable than are the analogous compositions of curves 140 and 150, respectively. In particular, the microbubbles having a lipid shell formed in a head space of perfluoropentane via the method of Example 2), shown in curve 120, show both the highest bubble production and the best bubbles stability over time. The microbubbles of Example 2 produce the most stable foam, wherein after an initial drop in height, the foam showed a negligible reduction in foam height between 2 days and 30 days.

Figure 2:
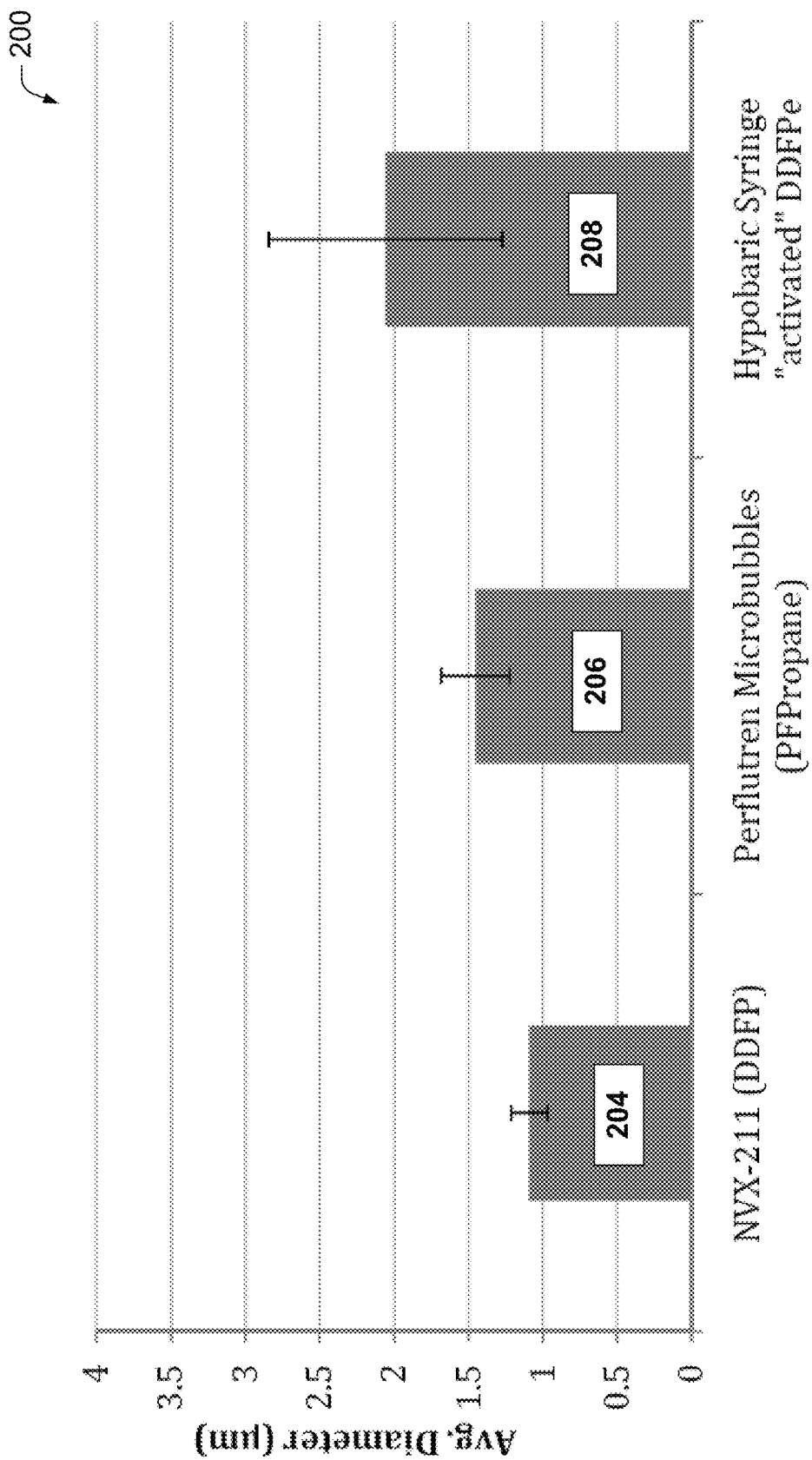
FIG. 2 graphically illustrates average diameters for microbubbles comprising different compositions and prepared using differing methods.

Referring to FIG. 2, chart 200 illustrates average bubble diameter for various microbubble compositions. The y-axis 202 represents average bubble diameter in micrometers. The average bubble diameter for each composition was measured using a FLOWCAM device sold in commerce by Fluid Imaging Technologies.

Bar 204 shows the average diameter of perfluoropentane filled microbubbles with a lipid shell formed in an atmosphere of perfluoropentane as described in Example 2. Bar 206 represents the average diameter of perfluoropropane filled microbubbles with a lipid shell formed in an atmosphere of perfluoropropane. The perfluoropropane microbubbles were formed using the method of Example 2, except that perfluoropropane was used instead of perfluoropentane.

Bar 208 represents the average diameter of perfluoropentane microbubbles formed by hypobaric activation. Hypobaric activation involves creating a lower pressure in a syringe by pulling back on the plunger of a sealed syringe containing a mixture of perfluoropentane and a stabilizing material. The resulting reduced pressure drop causes the liquid perfluoropentane droplets in solution to, at least in part, volatilize.

The data depicted in chart 200 is based on 5 individual test runs and the error bars on each bar 204, 206, and 208 represent 1 standard deviation about the mean. Those skilled in the art will appreciate that microbubbles having a smaller average diameter can more easily travel throughout the vascular system, and are therefore more desirable. As shown in chart 200, the average diameter of the microbubbles prepared according to Example 2 above, represented by bar 204, is about 1 micron. Applicant has found that microbubbles prepared using the composition and method of Example 2 comprise diameters less than 1.25 microns.

In contrast, microbubbles formed using the method of Example 2 but comprising perfluoropropane comprise an average diameter of about 1.5 microns. Even more significantly, microbubbles comprising perfluoropentane but formed using the hypobaric technique comprise an average diameter of about 2 microns. Applicants data shows that perfluoropentane-containing microbubbles formed using the method of Example 2 comprise about half the average diameter of perfluoropentane-containing microbubbles formed using the hypobaric technique.

In addition, the size distribution, as indicated by the error bars, is narrower for the microbubbles prepared according to Example 2 above, represented by bar 204, than the microbubbles produced via the other compositions and methods, represented by bars 206 and 208.

Figure 3:
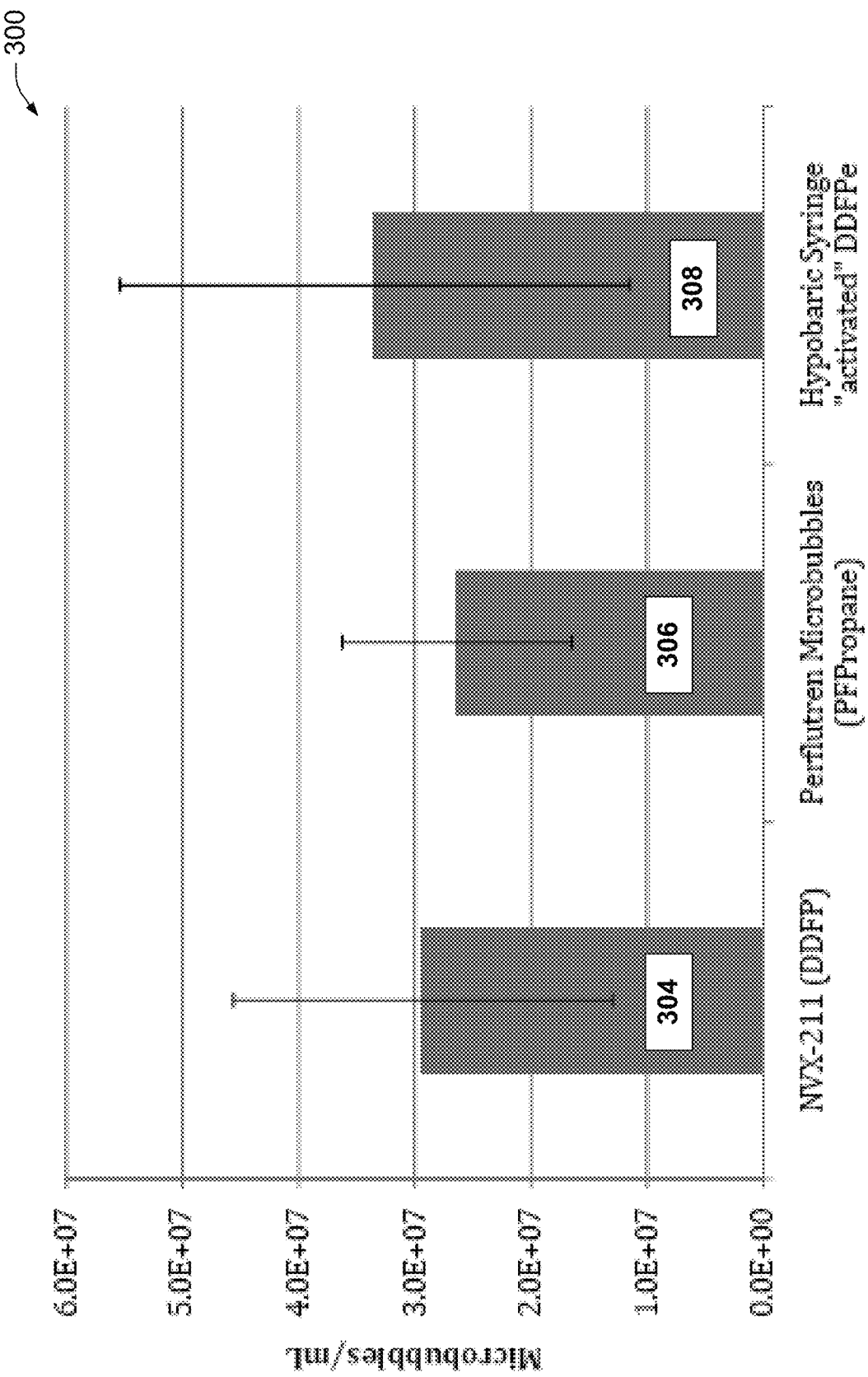
FIG. 3 graphically compares average densities for microbubble comprising different compositions and prepared using differing methods.

Referring to FIG. 3, chart 300 graphically illustrates the density of microbubbles for the microbubble compositions of FIG. 2. The bubble density for each composition was measured using a FLOWCAM device sold in commerce by Fluid Imaging Technologies.

Bar 304 graphically shows the microbubbles per mL for perfluoropentane filled microbubbles comprising a lipid shell formed in an atmosphere of perfluoropentane using the method described in Example 2 above. Bar 306 graphically shows the microbubbles per mL for perfluoropropane filled microbubbles comprising a lipid shell. The perfluoropropane microbubbles were formed using the method of Example 2, except that head space was filled with perfluoropropane rather than perfluoropentane.

Bar 308 represents the average density of perfluoropentane microbubbles formed by hypobaric activation. The data depicted in chart 300 is based on 5 individual test runs and the error bars on each bar 304, 306, and 308 represent 1 standard deviation about the mean.

While specific values have been recited for the various embodiments recited herein, it is to be understood that, within the scope of the invention, the values of all parameters, including amounts and ratios, may vary over wide ranges to suit different applications.

While the invention is described through the above-described exemplary embodiments, it will be understood by those of ordinary skill in the art that modifications to, and variations of, the illustrated embodiments may be made without departing from the inventive concepts disclosed herein. For example, although some aspects have been described with reference to a method, those skilled in the art should readily appreciate that functions, operations, decisions, etc. of all or a portion of each step, or a combination of the steps, of the method may be combined, separated into separate steps or performed in other orders. In addition, although a contrast agent has been described, the disclosed methods and formulations may be used for other purposes. Furthermore, disclosed aspects, or portions of these aspects, may be combined in ways not listed above. Accordingly, the invention should not be viewed as being limited to the disclosed embodiment(s).

We claim:

1. A method of forming a plurality of microbubbles, consisting of:
    disposing in a container comprising a first volume at ambient pressure, a second volume of a mixture comprising dipalmitoylphosphatidylcholine, wherein said first volume is greater than said second volume;
    sealing said container with a septum;
    inserting a needle through the septum and evacuating a headspace of said sealed container at 400 Torr;
    cooling said sealed container to about 4° C.;
    introducing liquid perfluoropentane into said sealed container using a frozen, gas tight syringe;
    evacuating a headspace in said sealed container using a needle inserted through said septum at 400 Torr until said liquid perfluoropentane is volatilized; and
    shaking the container to form said plurality of microbubbles, wherein each of said plurality of microbubbles comprises a diameter less than about 1.25 microns.

2. The method of claim 1, wherein the mixture further comprises dipalmitoylphosphatidylethanolaminepolyethylene glycol and dipalmitoylphosphatidic acid.

3. The method of claim 2, wherein the ratio of dipalmitoylphosphatidylcholine, dipalmitoylphosphatidylethanolaminepolyethylene glycol, and dipalmitoylphosphatidic acid is about 82 mole percent, 10 mole percent, and 8 mole percent, respectively.

4. The method of claim 3, wherein evacuating comprises reducing the pressure in said sealed container to a pressure of 400 Torr for 20 minutes.

5. The method of claim 4, wherein shaking comprises placing the container on a mechanical shaker set at about 75 Hz for about 45 seconds.

6. A method of forming a plurality of microbubbles, consisting of:
    disposing in a container comprising a first volume at ambient pressure, a second volume of a mixture comprising dipalmitoylphosphatidylcholine, wherein said first volume is greater than said second volume;
    forming a first gas by volatizing, external to said container, a liquid perfluorocarbon having a boiling point less than about 57° C. at 760 mm pressure;
    injecting said first gas into said container;
    sealing said container with a septum;
    injecting a second gas into said container, wherein said second gas is selected from the group consisting of air, nitrogen and oxygen; and
    shaking said container to form said plurality of microbubbles, wherein each of said plurality of microbubbles comprises a diameter less than about 1.25 microns.

7. The method of claim 6, wherein the mixture further comprises dipalmitoylphosphatidylethanolaminepolyethylene glycol and dipalmitoylphosphatidic acid.

8. The method of claim 7, wherein the ratio of dipalmitoylphosphatidylcholine, dipalmitoylphosphatidylethanolaminepolyethylene glycol, and dipalmitoylphosphatidic acid is about 82 mole percent, 10 mole percent, and 8 mole percent, respectively.

9. The method of claim 8, wherein the ratio of said first gas to said second gas is between about 80 mole percent to about 20 mole percent.

10. The method of claim 9, wherein shaking comprises placing the container on a mechanical shaker set at about 75 Hz for about 45 seconds.

* * * * *